(12) United States Patent
Zhang et al.

(10) Patent No.: US 9,844,676 B2
(45) Date of Patent: Dec. 19, 2017

(54) SYSTEMS, APPARATUS AND METHODS FACILITATING COMMUNICATION BETWEEN AN IMPLANTABLE DEVICE AND AN EXTERNAL DEVICE

(71) Applicant: Medtronic, Inc., Minneapolis, MN (US)

(72) Inventors: Bo Zhang, Blaine, MN (US); Matthew R. Yoder, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 14/837,948

(22) Filed: Aug. 27, 2015

(65) Prior Publication Data
US 2017/0056677 A1    Mar. 2, 2017

(51) Int. Cl.
*A61N 1/372* (2006.01)
*A61B 5/00* (2006.01)
*H04W 84/20* (2009.01)

(52) U.S. Cl.
CPC ........ *A61N 1/37211* (2013.01); *A61B 5/0002* (2013.01); *A61B 5/686* (2013.01);
(Continued)

(58) Field of Classification Search
USPC .......................................................... 607/16
See application file for complete search history.

(56) References Cited

U.S. PATENT DOCUMENTS 5,919,216 A * 7/1999 Houben ............. A61B 5/14532
607/72
9,009,805 B1 * 4/2015 Kirkby ............... G06K 9/00711
709/203
(Continued)

FOREIGN PATENT DOCUMENTS

EP          2878334           6/2015
EP          2991239 A1 *      3/2016
(Continued)

OTHER PUBLICATIONS

Townsend et al., "Getting Started with Bluetooth Low Energy: Tools and Techniques for Low Energy," O'Reilly Media, Inc. Apr. 30, 2014, pp. 48-50.*
(Continued)

*Primary Examiner* — Kennedy Schaetzle

(57) ABSTRACT

Techniques for facilitating communication between an implantable device and an external device are provided. In one example, an implantable device includes a data packet component and a communication component. The data packet component can insert information associated with the implantable device in a defined service field of an advertising data packet. The defined service field can be selected from one or more service fields of the advertising data packet based on the information associated with the implantable device. The communication component can transmit the advertising data packet. The external device can include a scanning component that can scan one or more service fields of the advertising data packet via an advertising communication channel, and a communication component that can establish a communication link with the implantable device in response to a determination that a criterion associated with a service field is satisfied.

28 Claims, 11 Drawing Sheets

(52) U.S. Cl.
CPC ..... *A61N 1/37252* (2013.01); *A61N 1/37276* (2013.01); *H04W 84/20* (2013.01)

(56) References Cited

U.S. PATENT DOCUMENTS

| | | | |
|---|---|---|---|
| 2003/0055464 A1* | 3/2003 | Darvish | A61N 1/05 607/40 |
| 2003/0208242 A1* | 11/2003 | Harel | A61B 5/04 607/40 |
| 2013/0214909 A1* | 8/2013 | Meijers | H04W 4/008 340/10.5 |
| 2014/0113558 A1 | 4/2014 | Varoglu et al. | |
| 2014/0133656 A1* | 5/2014 | Wurster | H04L 9/0637 380/270 |
| 2014/0188348 A1* | 7/2014 | Gautama | B60W 10/30 701/48 |
| 2014/0274127 A1 | 9/2014 | Beidel | |
| 2014/0370917 A1 | 12/2014 | Buchheim et al. | |
| 2015/0065047 A1 | 3/2015 | Wu et al. | |
| 2015/0099467 A1 | 4/2015 | Kang | |
| 2015/0296329 A1* | 10/2015 | Mao | H04W 4/008 370/338 |
| 2016/0259855 A1* | 9/2016 | Jwa | H04L 67/1095 |
| 2016/0278016 A1* | 9/2016 | Wang | H04W 52/0229 |
| 2016/0327631 A1* | 11/2016 | Salokannel | G01S 5/12 |
| 2017/0026777 A1* | 1/2017 | Denboer | H04W 4/008 |

FOREIGN PATENT DOCUMENTS

| | | |
|---|---|---|
| WO | 2011094075 | 8/2011 |
| WO | 2015069797 | 5/2015 |

OTHER PUBLICATIONS

Leach, P., et al., "A Universally Unique IDentifier (UUID) URN Namespace," Network Working Group, Jul. 2005, 33 pages, http://tools.ietf.org/html/rfc4122.

"Specification Adopted Documents," Bluetooth.org, 2015, 8 pages, https://www.bluetooth.org/en-us/specification/adopted-specifications, Last accessed Aug. 28, 2015.

"Tutorial: How to Create a Custom Bluetooth Smart Embedded Application with the CC2650DK," Texas Instruments Wiki, Last modified Aug. 18, 2015, 19 pages, http://processors.wiki.ti.com/index.php/Tutorial:_How_to_Create_a_Custom_Bluetooth_Smart_Embedded_Application_with_the_CC2650DK, Last accessed Aug. 28, 2015.

"Universally unique identifier," Wikipedia, Last modified Aug. 14, 2015, 6 pages, https://en.wikipedia.org/wiki/Universally_unique_identifier, Last accessed Aug. 28, 2015.

"General Description" from Specification of the Bluetooth System, Version 4.2, Bluetooth SIG Proprietary, Dec. 2, 2014, vol. 1, Part A, pp. 13-19.

PCT/US2016/045690, Invitation to pay additional fees and partial ISR dated Nov. 16, 2016, 8 pages.

C00011220.WOU2 (PCT/US2016/045690) PCT Notification of Transmittal of the International Search Report and the Written Opinion of the International Searching Authority, dated Jan. 24, 2017, 20 pages.

* cited by examiner

SYSTEMS, APPARATUS AND METHODS FACILITATING COMMUNICATION BETWEEN AN IMPLANTABLE DEVICE AND AN EXTERNAL DEVICE

TECHNICAL FIELD

This disclosure generally relates to facilitating communication between an implantable device and an external device.

BACKGROUND

Modern healthcare facilitates the ability for patients to lead healthy and full lives. Implantable medical devices (IMDs) are often utilized for such medical advances. For example, IMDs such as pacemakers, implantable cardioverter-defibrillators (ICDs), neurostimulators, and drug pumps can facilitate management with a wide range of ailments, including, but not limited to, cardiac arrhythmias, diabetes, and Parkinson's disease. Patients and medical care providers can monitor the IMD and assess a patient's current and historical physiological state to identify and/or predict impending events or conditions.

Implantable devices, including IMDs, are increasing in complexity while shrinking in size. One hurdle to achieving such small and highly functional devices is efficient power management of these devices. In particular, many implantable devices operate from power sources that have a limited lifespan and/or are not rechargeable. As such, after the implantable device is implanted within the human body and the lifespan of the power source has been reached, the implantable device may need to be removed. Numerous processes associated with an implantable device directly impact life of a power source of the implantable device. For example, a communication connection process between an implantable device and an external device is generally inefficient and can unnecessarily drain power from a power source of the implantable device if not properly managed. Thus, extending life of a power source of an implantable device by improving a communication connection process between an implantable device and an external device is highly desirable.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, apparatus, methods and computer-readable storage media facilitating communication between an implantable device and an external device. In some embodiments, the implantable device is or includes an IMD. In other embodiments, the implantable device is or includes a device configured to interact with the IMD. In these embodiments, both the implantable device and the IMD can be implanted within a patient.

In one embodiment, an implantable device is provided. The implantable device can include: a memory that stores executable components; and a processor coupled to the memory and configured to execute the executable components stored in the memory. The executable components can include a data packet component and a communication component. The data packet component is configured to insert information associated with the implantable device in a defined service field of an advertising data packet. In some embodiments, the defined service field is selected from one or more service fields of the advertising data packet based on the information associated with the implantable device. The communication component is configured to transmit the advertising data packet.

In various different embodiments, the data packet component is configured to encode the information associated with the implantable device as a universally unique identifier (UUID), a set of hexadecimal values and/or a bit value that is greater than or equal to a 16-bit value.

In some embodiments, the data packet component is configured to insert information indicative of a status of the implantable device in the defined service field of the advertising data packet. As used herein, the term "status" can include a state of, alert associated with, an indicator of and/or a fault condition for an implantable device 104. In some embodiments, the data packet component is configured to insert information associated with a presence of the implantable device in the defined service field of the advertising data packet. In some embodiments, the communication component is configured to sequentially transmit the advertising data packet via a set of advertising communication channels.

In another embodiment, an apparatus is provided. In some embodiments, the apparatus can be the above-referenced external device. The apparatus can include a memory that stores executable components; and a processor coupled to the memory and configured to execute the executable components stored in the memory. The executable components can include a scanning component and a communication component. The scanning component can be configured to scan one or more service fields of an advertising data packet associated with an implantable device via an advertising communication channel. The communication component can be configured to establish a communication link with the implantable device via a communication channel different than the advertising communication channel. The communication link can be established in response to a determination that a criterion associated with a service field of the one or more service fields is satisfied.

In some embodiments, the scanning component is further configured to identify one or more unique identifiers included in the advertising data packet and/or to scan for a defined one of the one or more service fields via the advertising communication channel.

In some embodiments, the communication component is further configured to establish the communication link in response to a determination that information indicative of a status of the implantable device is included in the service field. The communication component can also be configured to establish the communication link in response to a determination that information associated with a presence of the implantable device is included in the service field.

In yet another embodiment, a method is provided. The method can include determining, by a device including a processor, information associated with an implantable device; and selecting a service field of an advertising data packet from a set of service fields of the advertising data packet based on the information associated with the implantable device. The method can also include inserting the information associated with the implantable device into the service field of the advertising data packet; and transmitting the advertising data packet.

In some embodiments, the inserting includes encoding the information associated with the implantable device as a universally unique identifier, as a set of hexadecimal values and/or as a bit value that is greater than or equal to a 16-bit value. In some embodiments, the encoding includes encoding information indicative of a status of the implantable device in the service field of the advertising data packet. In some embodiments, the inserting includes encoding information indicative of medical data associated with the implantable device in the service field of the advertising data packet.

In yet another embodiment, a system is provided. The system includes an apparatus and an electronic device. In some embodiments, the apparatus is configured to select a service field of an advertising data packet from one or more service fields of the advertising data packet based on a status of an implantable device; generate information indicative of the status of the implantable device in the service field of the advertising data packet; and transmit the advertising data packet during a defined interval of time. The electronic device is configured to scan for the one or more services fields of the advertising data packet associated with the implantable device; and establish a communication link with the implantable device in response to a determination that the information indicative of the status of the implantable device is included in the service field.

In some embodiments, the apparatus is configured to receive information of the one or more service fields from a server. The apparatus and/or a memory within the apparatus is updated with the information of the one or more service fields received from the server. The server can be configured to randomly generate information of the one or more service fields in some embodiments. In some embodiments, the apparatus is configured to transmit the advertising data packet utilizing the Bluetooth Low Energy communication protocol.

In some embodiments, the system can also include a server communicatively coupled to the apparatus and configured to randomly generate information for the one or more service fields. In some embodiments, the electronic device is configured to receive the information for the one or more service fields from a server.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
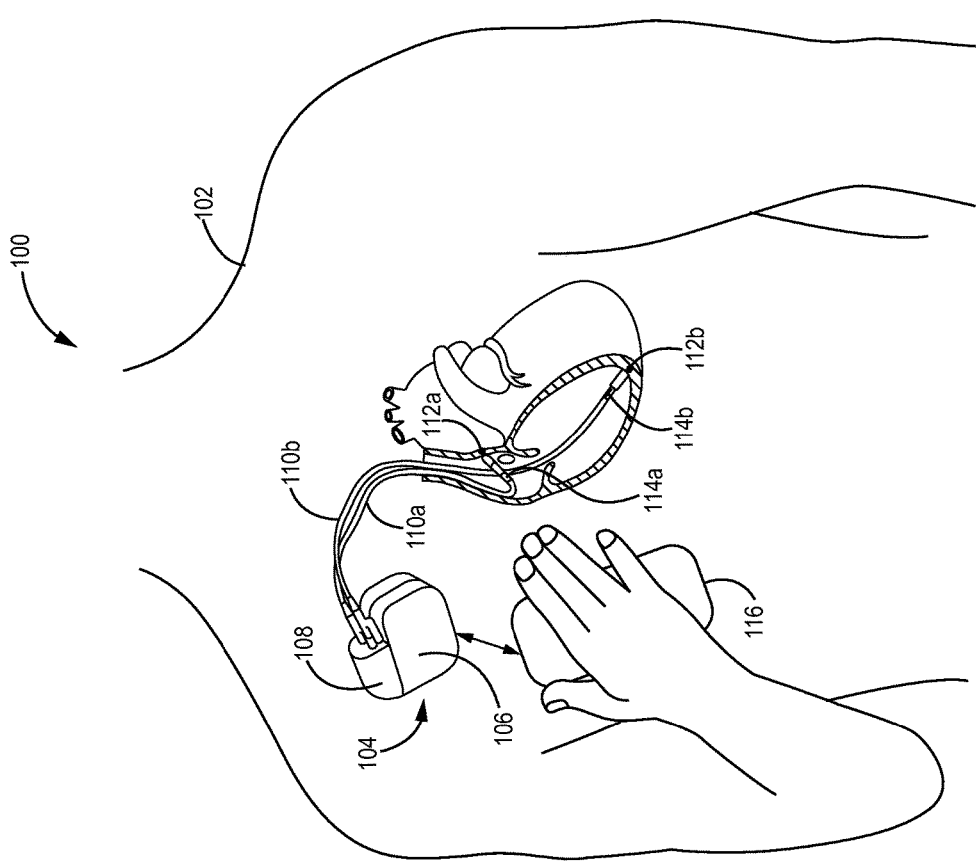
FIG. 1 illustrates a schematic diagram of an example, non-limiting medical device telemetry system facilitating communication between an implantable device and an external device in accordance with one or more embodiments described herein.

With reference now to the drawings, FIG. 1 illustrates a schematic diagram of an example, non-limiting medical device telemetry system 100 facilitating communication between an implantable device and an external device in accordance with one or more embodiments described herein. In the embodiment shown, medical device telemetry system 100 includes an implantable device 104 implanted within a body 102, and an external device 116. Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

One or more embodiments of medical device telemetry system 100 are described in connection with facilitating communication between the implantable device 104 and the external device 116. The implantable device 104 can insert information associated with the implantable device 104 into a field of an advertising data packet. For example, the implantable device 104 can encode and/or generate information associated with the implantable device 104 into a field of an advertising data packet. In some embodiments, the implantable device 104 is an IMD that is also configured to facilitate one or more diagnostic or treatment functions relative to the body 102. In one embodiment, the implantable device 104 is separate from an IMD (not shown in this embodiment) that is also implanted within the body 102 and communicatively and/or electrically coupled to the IMD.

An advertising data packet can be a data packet employed for advertising. For example, an implantable device (e.g., the implantable device 104) can broadcast certain data to share with other devices via an advertising data packet. An advertising packet can include one or more types or sections of data that include useful information for other devices in close proximity to an implantable device (e.g., the implantable device 104) that broadcasts the advertising data packet. The advertising data packet can include a header portion and a portion that can be read by other devices to determine whether the device should connect to the implantable device. In some cases, an advertising data packet is employed by an implantable device to make the presence of an implantable device known to other devices in close proximity to the implantable device (e.g., to help other devices discover the implantable device). Therefore, an advertising data packet can broadcast information (e.g., from the implantable device 104) to one or more devices within a particular distance from the implantable device 104. In this regard, the advertising data packet can facilitate discovery of one or more devices within a certain distance from the implantable device 104.

Accordingly, in some embodiments, an advertising data packet can facilitate a connection between the implantable device 104 and a device that receives the advertising data packet based on the information included in the advertising data packet. For example, a particular field associated with an advertising data packet can be selected from a set of fields based on the information associated with the implantable device 104. That particular information can be inserted into a particular field (e.g., service field) associated with an advertising data packet by being stored in, encoded and/or generated in the particular field. In some embodiments, the implantable device 104 can be configured to packetize the information associated with the implantable device 104 and/or other information to facilitate generation of the advertising data packet. For example, a set of bytes of information included in a payload portion (e.g., a packet data unit) of the advertising data packet can correspond to the information associated with the implantable device 104. In some embodiments, the advertising data packet can additionally include other sets of bytes associated with other portions of the advertising data packet (e.g., a header portion, an address portion, another payload portion, etc.). In some embodiments, the implantable device 104 can include a packet generator component (not shown) configured to facilitate generation of an advertising data packet that includes a field (e.g., service field) that corresponds to the information associated with the implantable device 104.

The implantable device 104 can include one or more devices, transducers and/or circuits that can convert information from one format to another format. In some embodiments, the implantable device 104 can include a device, transducer and/or circuit that can convert a signal associated with a status of the implantable device 104 (or, in embodiments in which the implantable device 104 is an IMD, alternatively or additionally, the status of the IMD) to information for transmission by the implantable device 104 (or generally to another signal of any number of different formats suitable for reception by the external device 116).

The content of the field (e.g., the service field) in the advertising data packet can be dynamic and can be changed from time to time. In some embodiments, the content of the field can vary based on a status of the implantable device 104. For example, a status of the implantable device 104 can be information associated with, detected by and/or determined by the implantable device 104. For example, in response to a determination regarding particular information associated with and/or detected by the implantable device 104, a particular field can be selected (e.g., from a set of fields). Furthermore, the particular information can be added to an advertising data packet, for example, by encoding the particular information in the advertising data packet and/or by generating the advertising data packet. Furthermore, in response to another determination that other particular information is associated with and/or detected by the implantable device 104, another field can be selected (e.g., from a set of fields). Furthermore, the other particular information can be added to an advertising data packet, for example, by encoding the other particular information in the advertising data packet and/or by generating the advertising data packet.

In some embodiments, for example, the implantable device 104 can employ a table that maps information associated with a status of the implantable device 104 to a particular field (e.g., a particular service field) for an advertising data packet. For example, a table (e.g., a mapping table) can include one or more fields and one or more respective portions of information that can be associated with, detected by and/or determined by the implantable device 104. The implantable device 104 can map the actual information associated with a status of the implantable device 104 to the particular field based on the field indicated in the table for the particular information. As described above, the table information and/or mapping can be changed from time to time based on any number of different events or conditions including, but not limited to, new mapping information being received at the implantable device 104 from a source external to the body 102 of the patient or the like.

In some embodiments, the implantable device 104 can be configured to select a field (e.g., a service field) of an advertising data packet from a set of fields (e.g., a set of service fields) of the advertising data packet based on the information associated with the implantable device 104. By way of example, but not limitation, in some embodiments, the particular field selected can communicate one or more different aspects or types of information. For example, in some embodiments, a set of fields can be generated for the implantable device 104 (in some embodiments, the set of fields generated for different implantable devices can differ from one another). The implantable device 104 can select one or more of the possible fields from the set of fields for the implantable device 104 to employ in advertisement of the advertising data packet. The particular fields selected by the implantable device 104 can be selected based on the status of the implantable device 104 in some embodiments.

In some embodiments, the fields (e.g., the service fields) can be UUID fields. A UUID field can be an identifier configured as a defined sequence of bits and/or a defined string representation of a sequence of bits. In some embodiments, a UUID field can be a fixed size (e.g., 16 bits, 32 bits, 64 bits, 128 bits, another set of octets, etc.). In one embodiment, a UUID field can include a fixed portion, which can include a fixed set of bits, and a dynamic portion, which can include a dynamic set of bits. In some embodiments, a UUID field can include a set of subfields.

In various embodiments, one or more (or, in some embodiments, each) field from a set of possible fields can be configured to represent unique information associated with the implantable device 104. For example, a field (e.g., a service field) can be configured to represent a status of the implantable device 104. Additionally or alternatively, a field (e.g., a service field) can be configured to represent a power status associated with the implantable device 104. For example, a service field can be configured to represent a status of one or more power sources associated with and/or included in the implantable device 104. In one embodiment, a status of a power source can be an indication of remaining battery life, for example. Additionally or alternatively, a field (e.g., a service field) can be configured to represent medical data associated with the implantable device 104, remote monitoring data associated with the implantable device 104, patient data associated with the implantable device 104 or other data associated with the implantable device 104. For example, medical data can include medical data read or otherwise obtained by the implantable device 104, electrical signals sensed and/or generated by the implantable device 104, a voltage or current provided by the implantable device 104 and/or a medical dosage provided by the implantable device 104. Patient data can include, for example, a name of a patient, a date of birth of a patient, a medical history associated with a patient, a medical identification or number associated with the patient or the like. Remote monitoring data can include, for example, analysis data associated with the implantable device 104 and/or a patient, monitoring data for a condition associated with the implantable device 104 and/or the body 102 of the patient.

In some embodiments, the implantable device 104 can insert information indicative of the information associated with the implantable device 104 into the field of the advertising data packet (e.g., generate and/or encode information indicative of the information associated with the implantable device 104 in the field of the advertising data packet), and transmit the advertising data packet that includes the information associated with the implantable device 104. For example, the implantable device 104 can broadcast the advertising data packet that includes the information associated with the implantable device 104 during a defined interval of time. As such, in some embodiments, another device (e.g., the external device 116) can be provided an opportunity to receive the advertising data packet during the defined interval of time. In one example, the implantable device 104 can generate the advertising data packet as a binary frequency modulation signal.

It is to be appreciated that the implantable device 104 can include one or more devices, transducers and/or circuits that can facilitate transmittal of the advertising data packet. For example, the implantable device 104 can include a transmitter that transforms electrical power into a signal associated with the advertising data packet. Additionally, the implantable device 104 can include one or more devices, transducers and/or circuits that can facilitate receiving information from one or more devices (e.g., the external device 116, a server, etc.). For example, the implantable device 104 can include a receiver that transforms a signal into electrical power.

The external device 116 can scan for the set of fields of the advertising data packet associated with the implantable device 104 (e.g., without connecting to the implantable device 104). For example, the external device 116 can include a receiver that can monitor for the advertising data packet generated by the implantable device 104. As such, if the external device 116 is within a certain range from the implantable device 104 and detects the advertising data packet, the external device 116 can obtain the information associated with the implantable device 104 and inserted into the advertising data packet without connecting to the implantable device 104.

Furthermore, the external device 116 can establish a communication link with the implantable device 104 in response to a determination that the information determined during the monitoring (which is indicative of the information associated with the implantable device 104) is included in the field. For example, in some embodiments, the external device 116 only connects to the implantable device 104 when an advertising data packet indicates a request for communication (e.g., between the implantable device and an external device, such as the external device 116). After establishment of the communication link between the implantable device 104 and the external device 116, in some embodiments, the external device 116 and the implantable device 104 can exchange one or more data packets. For example, when a communication link is established between the external device 116 and the implantable device 104 (e.g., in response to detection by the external device 116 of an advertising data packet that includes information associated with the implantable device 104), the external device 116 can communicate with the implantable device 104 to exchange data with the implantable device 104. In a non-limiting example, the external device 116 can read data captured by the implantable device 104 (e.g., electrogram data). The implantable device 104 may also transmit sensed physiological data, diagnostic determinations made based on the sensed physiological data, implantable device 104 performance data and/or implantable device 104 integrity data to the external device 116. Moreover, in some embodiments, if the external device 116 does not identify an advertising data packet generated by the implantable device 104, a communication link is not established between the external device 116 and the implantable device 104 (e.g., since the external device 116 awaits identification of an advertising data packet before starting a telemetry session with the implantable device 104). Accordingly, the frequency and/or number of unnecessary connections between the implantable device 104 and the external device 116 can be reduced, thereby conserving power of the power source of the implantable device 104. Moreover, information associated with the implantable device 104 can be indicated to an external device using minimal power consumption, e.g., by not requiring a communication session to be established by the implantable device 104 to receive information, but instead receiving information associated with the implantable device 104 within the advertising packet itself. Further, in some embodiments, the processor and/or memory operations of the implantable device 104 and/or the external device 116 can be made to be more efficient due to reduction in processes for unnecessary connections between the external device 116 and the implantable device 104.

Information associated with the implantable device 104 can also be provided to a wide variety of external devices, including, but not limited to, a tablet computer associated with a patient or a physician, a smartphone associated with a patient or a physician, a medical device associated with a patient or a physician, an electronic device at a home of a patient or at an office of a physician, an off-the-shelf device purchased at a store, etc. Additionally, in some embodiments, compatibility between the implantable device 104 and external devices can be increased by allowing the information associated with the implantable device 104 to be included in an advertising data packet that can be received by any external device through the utilization of a communication protocol, such as, but not limited to, the BLUETOOTH® low energy communication protocol.

In the example shown in medical device telemetry system 100, a person operating the external device 116 is a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of implantable devices configured to communicate with the external device 116 or another external device. The particular, size, shape, placement and/or function of the implantable device 104 may not be critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110a,b connected to the housing 106. The leads 110a,b extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. When implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108.

In one or more embodiments, the implantable device 104 is configured to deliver therapy to the heart (or other location) via the electrical conductors to one or more of electrodes 112a,b and 114a,b. In the case of pacing therapy, for example, the implantable device 104 may deliver pacing pulses via a unipolar electrode configuration, e.g., using electrodes 112a,b and a housing electrode of the implantable device 104. In other instances, the implantable device 104 may deliver pacing pulses via a bipolar electrode configuration, e.g., using electrodes 112a,b and ring electrodes 114a,b. Implantable device 104 may also receive sensed electrical signals on the electrical conductors from one or more of electrodes 112a,b and 114a,b. The implantable device 104 may sense the electrical signals using either a unipolar or bipolar electrode configuration.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or underneath or below the sternum. Example extravascular ICDs having subcutaneous electrodes are described in U.S. Patent Publication No. 2014/0214104 (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances, take the form of a coil. The implantable device 104 can deliver defibrillation or cardioversion shocks to the heart via any combination of the elongated electrodes and housing electrode. As another example, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (Kenneth), and U.S. Patent Publication No. 2014/0214104 (Greenhut et al.), each of which is incorporated herein in its entirety. In the case of a leadless pressure sensor, the device may include a housing having a fixation member and a pressure sensing component. One example of a leadless pressure sensor is described in U.S. Patent Publication No. 2012/0108922 (Schell et al.), which is incorporated herein in its entirety.

External device 116 can include any suitable computing device configured to communicate with implantable device 104. In some embodiments, the external device 116 can be a remote electronic device. For example, external device 116 can include, but is not limited to, a handheld computing device, a mobile phone, a smart phone, a tablet personal computer (PC), a laptop computer, a desktop computer, a personal digital assistant (PDA) and/or a wearable device. In some embodiments, the external device 116 can include a display that can present information associated with the implantable device 104. In another embodiment, the external device 116 can include an application and/or a program associated with the implantable device 104.

Figure 2:
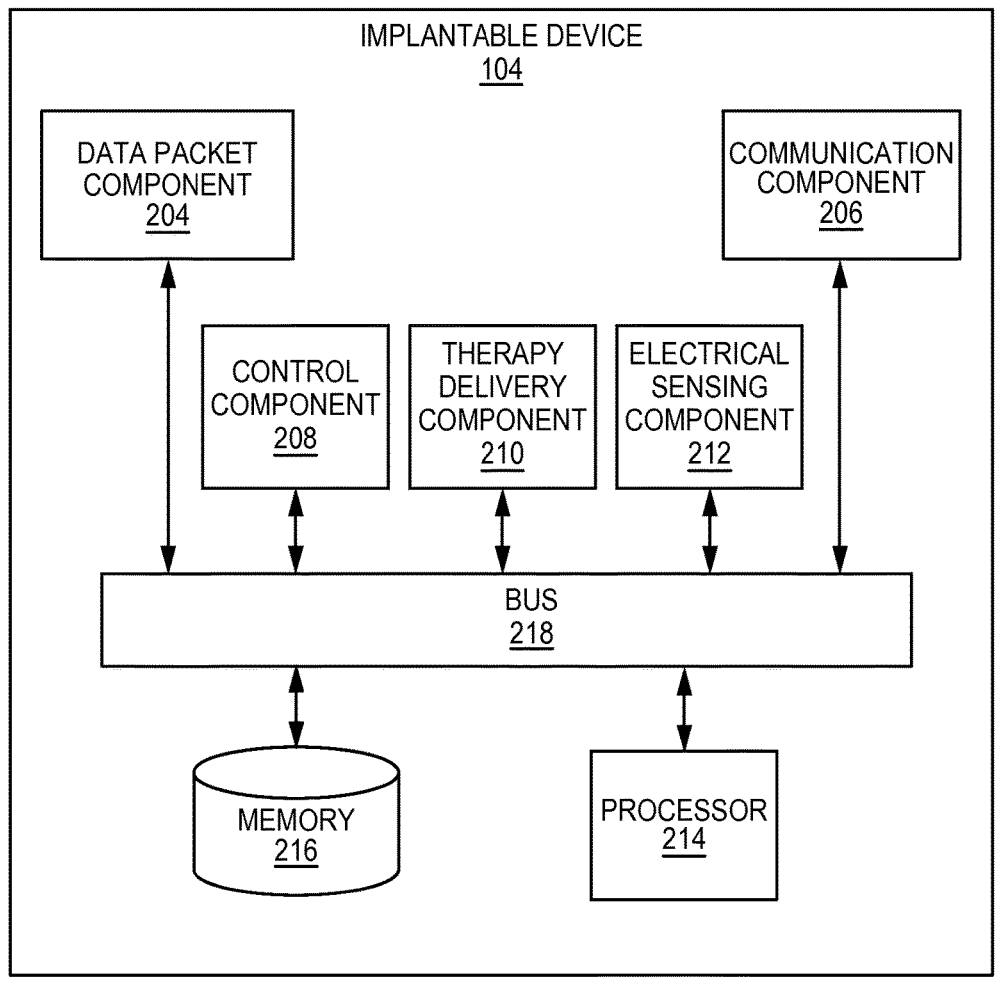
FIG. 2 illustrates a block diagram of an example, non-limiting implantable device in accordance with one or more embodiments described herein.

FIG. 2 illustrates a block diagram of an example, non-limiting implantable device (e.g., implantable device 104) in accordance with one or more embodiments described herein. The implantable device 104 includes a data packet component 204, a communication component 206, a control component 208, a therapy delivery component 210 and/or an electrical sensing component 212. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Implantable device 104 can include memory 216 for storing computer executable components and instructions. Implantable device 104 can further include a processor 214 to facilitate operation of the instructions (e.g., computer executable components and instructions) by implantable device 104. Implantable device 104 can include a bus 218 that couples the various components of the implantable device 104, including, but not limited to, the data packet component 204, the communication component 206, the control component 208, the therapy delivery component 210, the electrical sensing component 212, the processor 214 and/or the memory 216. Repetitive description of like elements employed in other embodiments described herein is omitted for sake of brevity.

The data packet component 204 can insert information associated with the implantable device 104 into a field of an advertising data packet (e.g., the data packet component 204 can encode information associated with the implantable device 104). Additionally or alternatively, the data packet component 204 can generate information associated with the implantable device 104. In one example, the data packet component 204 can determine the information associated with the implantable device 104. For example, in an implementation, the data packet component 204 can retrieve the information (e.g., the information associated with the implantable device 104) from memory (e.g., memory 216), the control component 208 or the electrical sensing component 212. In another example, the data packet component 204 can receive the information associated with the implantable device 104 from another component included in the implantable device 104. By way of example, but not limitation, a detection component of an IMD, for example, can detect and/or read one or more signals or other measurement data that can then be obtained by the data packet component 204.

The information can be inserted into a defined service field of an advertising data packet (e.g., the information can be encoded as a defined service field of an advertising data packet). Additionally or alternatively, the information can be generated as a defined service field of an advertising data packet For example, the communication component 206 can include a packet generator, a transmitter, a frequency modulator, and/or other circuitry configured to generate the advertising data packet based on the information associated with the implantable device 104 (e.g., the information encoded and/or generated by the data packet component 204). In one example, the information can be encoded as a UUID field that is associated with a packet data unit of the advertising data packet. The UUID field can be an identifier configured as a defined sequence of bits and/or a defined string representation of a sequence of bits. The UUID field can also be a fixed size (e.g., 16 bits, 32 bits, 64 bits, 128 bits, another set of octets, etc.). In one embodiment, the UUID field can include a fixed portion (e.g., a fixed set of bits) and a dynamic portion (e.g., a dynamic set of bits). In another embodiment, the UUID field can include a set of subfields.

The advertising data packet can be configured for transmission over an advertising communication channel. In some embodiments, the advertising communication channel can be a communication channel that is associated with a particular frequency employed for broadcast of information. In various embodiments, the advertising communication channel described herein can be a 2402 megahertz (MHz) communication channel, a 2426 MHz communication channel and/or a 2480 MHz communication channel. The particular frequencies provided are mere examples and, in other embodiments, the advertising communication channel can be located at any number of other different frequencies.

The data packet component 204 can select the defined service field from one or more service fields based on the information associated with the implantable device 104. For example, a set of defined service fields (e.g., a set of defined UUIDs) can be generated for the implantable device 104. The data packet component 204 can therefore select a defined service field (e.g., a particular UUID) from the set of defined service fields based on the information associated with the implantable device 104. In one example, the data packet component 204 can employ a data structure (e.g., a table data structure or a mapping data structure) that maps one or more (or, in some embodiments, each) possible service field from the set of defined service fields to information associated with the implantable device 104. The data structure can be stored, for example, in the memory 216 and/or in another memory. In one example, the data packet component 204 can encode the information associated with the implantable device 104 as a set of hexadecimal values that represents a UUID. For example, the information associated with the implantable device 104 can be encoded as a hexadecimal value. In another example, the data packet component 204 can encode the information associated with the implantable device 104 as a bit value (e.g., a 16-bit value, a 32-bit value, a 64-bit value, 128-bit value, etc.) that represents a UUID.

In some embodiments, an encoded representation of the information associated with the implantable device 104 can be received from another device in communication with the data packet component 204. For example, encoded content (e.g., an encoded representation) of at least one service field from the set of defined service fields can be received from another device in communication with the data packet component 204. The other device can be, for example, a server located external to the body in which the data packet component 204 is located. In some embodiments, encoded content (e.g., an encoded representation) of at least one service field from the set of defined service fields can be randomly generated by the data packet component 204. In yet another embodiment, encoded content (e.g., an encoded representation) of at least one service field from the set of defined service fields can be pre-generated by the data packet component 204.

In some embodiments, the data packet component 204 can insert information indicative of a status of the implantable device 104 into a service field of an advertising data packet. For example, the data packet component 204 can encode and/or generate information indicative of a status of the implantable device 104 into a service field of an advertising data packet. Therefore, the data packet component 204 can select the defined service field from one or more service fields of the advertising data packet based on the status of the implantable device 104. For example, the data packet component 204 can select a defined service field (e.g., a particular UUID) from the set of defined service fields based on the status of the implantable device 104. As such, the data packet component 204 can encode and/or generate the status of the implantable device as a UUID. In an embodiment, the data packet component 204 can select a defined service field from the set of defined service field in response to determining a status of the implantable device 104.

In one example, the data packet component 204 can encode the information indicative of the status of the implantable device as a set of hexadecimal values that represents a UUID. In another example, the data packet component 204 can encode the information indicative of the status of the implantable device as a bit value (e.g., a 16-bit value, a 32-bit value, a 64-bit value, 128-bit value, etc.) that represents a UUID.

A status of the implantable device 104 can be, for example, a communication status of the implantable device 104. For example, a first status of the implantable device 104 can indicate that the implantable device 104 has information to send, and a second status of the implantable device 104 can indicate that the implantable device 104 has no information to send. A status of the implantable device 104 can be, for example, a device status of the implantable device 104. A device status of the implantable device 104 can include information, such as, but not limited to, power status information associated with the implantable device 104, a battery status associated with the implantable device 104, a processing status associated with the implantable device 104, a mode currently being implemented by the implantable device 104, other device status information associated with the implantable device 104, etc.

In another example, the data packet component 204 can additionally or alternatively insert information indicative of an alert into the selected service field of the advertising data packet (e.g., the data packet component 204 can additionally or alternatively encode and/or generate information indicative of an alert in the selected service field of the advertising data packet). As used herein, in various embodiments, the term "alert" can mean an indicator of a particular event, condition or other information or status. In some embodiments, an alert need not be limited to or include a fault condition. For example, the information associated with the implantable device 104 can be indicative of an alert or an indicator associated with a presence of the implantable device 104. Therefore, the external device 116 can be within a range to communicate with the implantable device 104 in response to receiving an advertising data packet that includes the alert or the indicator. In another example, the information associated with the implantable device 104 can be indicative of a fault status associated with the implantable device 104. A fault status can be, for example, a fault condition or an error condition associated with the implantable device 104.

The data packet component 204 can additionally or alternatively insert other information into the selected service field of the advertising data packet (e.g., the data packet component 204 can additionally or alternatively encode and/or generate other information in the selected service field of the advertising data packet). For example, the other information associated with the implantable device 104 can include device monitoring data, medical data (e.g., medical readings, remote monitoring data) associated with the implantable device 104, fitness data associated with the implantable device 104, patient data for a patient associated with the implantable device 104 (e.g., a name, address or other information for a patient), device data associated with the implantable device 104 (e.g., a model name of the implantable device 104, a serial number of the implantable device 104) and/or other data associated with the implantable device 104. The advertising data packet can include a set of bytes that corresponds to the information associated with the implantable device (e.g., the service field that corresponds to the information associated with the implantable device 104). The set of bytes that corresponds to the information associated with the implantable device 104 (e.g., the service field that corresponds to the information associated with the implantable device 104) can be included in a payload portion (e.g., a packet data unit) of the advertising data packet. The advertising data packet can additionally include other sets of bytes associated with other portions of the advertising data packet (e.g., a header portion, an address portion, another payload portion, etc.).

The communication component 206 can wirelessly transmit from the body 102 the advertising data packet that includes the information associated with the implantable device 104 (e.g., the status of the implantable device, an alert associated with the implantable device 104, an indicator associated with the implantable device 104, other data associated with the implantable device 104, etc.). In one example, the communication component 206 can transmit the advertising data packet that includes the information associated with the implantable device 104 during a defined period of time. In another example, the communication component 206 can transmit the advertising data packet one or more times during a defined period of time to advertise the advertising data packet to an external device (e.g., the external device 116).

In some embodiments, the communication component 206 can sequentially transmit the advertising data packet that includes the information associated with the implantable device 104 via two or more advertising communication channels. For example, the communication component 206 can sequentially transmit the advertising data packet via a first advertising communication channel (e.g., a 2402 MHz communication channel), a second advertising communication channel (e.g., a 2426 MHz communication channel) and/or a third advertising communication channel (e.g., a 2480 MHz communication channel).

In another example, the communication component 206 can concurrently transmit the advertising data packet that includes the information associated with the implantable device 104 via two or more of the advertising communication channels. For example, the communication component 206 can concurrently transmit the advertising data packet that includes the information associated with the implantable device 104 via a first advertising communication channel (e.g., a 2402 MHz communication channel), a second advertising communication channel (e.g., a 2426 MHz communication channel) and/or a third advertising communication channel (e.g., a 2480 MHz communication channel).

The communication component 206 can transmit the advertising data packet via an advertising communication channel associated with a communication protocol utilizing lower energy consumption than a conventional communication protocol for wirelessly transmitting data. In a non-limiting example, communication component 206 can transmit the advertising data packet via an advertising communication channel associated with a BLUETOOTH® low energy (BLE) protocol.

With reference to FIGS. 1 and 2, the communication component 206 can additionally or alternatively establish, via a communication channel different than the advertising communication channel associated with the advertising data packet, a wireless communication link with the external device 116 external to a body 102 in which the implantable device 104 is located. For example, the communication channel different than the advertising communication channel associated with the advertising data packet can be another communication channel configured for transmitting data to the implantable device 104 and/or receiving other data from the implantable device 104. In a non-limiting example, the external device 116 can read data captured by the implantable device 104 (e.g., electrogram data) via the communication channel different than the advertising communication channel. In another non-limiting example, the implantable device 104 can transmit sensed physiological data, diagnostic determinations made based on the sensed physiological data, implantable device 104 performance data and/or implantable device 104 integrity data to external device 116 via the communication channel different than the advertising communication channel.

In one embodiment, the implantable device 104 can connect to (e.g., actively communicate with) the external device 116, transmit data directly to the external device 116 and/or receive data from the external device 116 in response to a determination by the external device 116 that a criterion associated with a service field associated with the advertising data packet is satisfied. For example, the external device 116 can read data captured by the implantable device 104 (e.g., electrogram data) via the communication channel different than the advertising communication channel in response to a determination by the external device 116 that a criterion associated with a service field associated with the advertising data packet is satisfied. In another example, the implantable device 104 can transmit sensed physiological data, diagnostic determinations made based on the sensed physiological data, implantable device 104 performance data and/or implantable device 104 integrity data to external device 116 via the communication channel different than the advertising communication channel in response to a determination by the external device 116 that a criterion associated with a service field associated with the advertising data packet is satisfied. A criterion associated with a service field can be, for example, that the service field is included in a set of defined service fields associated with the implantable device 104.

In some embodiments, the communication component 206 can receive a response data packet from the external device 116 in response to receipt of the advertising data packet by the external device 116.

With reference to FIGS. 1 and 2, in some embodiments, the control component 208 can communicate with the therapy delivery component 210 and/or the electrical sensing component 212. For example, the control component 208 can communicate with the therapy delivery component 210 and/or the electrical sensing component 212 to facilitate sensing of cardiac electrical activity, detection of cardiac rhythms, and generation of electrical stimulation therapies in response to sensed signals. The therapy delivery component 210 can be, for example, electrically coupled to tip electrodes 112*a,b*, ring electrodes 114*a,b* and/or the housing 106 to deliver electrical stimulation therapies such as cardioversion-defibrillation (CV/DF) shocks. In some examples, the therapy delivery component 210 can be additionally coupled to tip electrodes 112a,b and/or ring electrodes 114a,b for use in delivering therapy and/or delivering mild electrical stimulation to generate a patient alert.

The electrical sensing component 212 can be electrically coupled to tip electrodes 112a,b and ring electrodes 114a,b carried by leads 110a,b and housing 106, which may serve as a common or ground electrode. The electrical sensing component 212 can be selectively coupled to tip electrodes 112a,b, ring electrodes 114a,b and/or the housing 106 in order to, for example, monitor electrical activity of the patient's heart (e.g., electrical activity associated with tip electrodes 112a,b and/or ring electrodes 114a,b). For example, the electrical sensing component 212 can include detection circuitry associated with tip electrodes 112a,b and/or ring electrodes 114a,b. In one embodiment, the electrical sensing component 212 can be enabled to monitor one or more sensing vectors selected from the tip electrodes 112a,b and/or the ring electrodes 114a,b. For example, the electrical sensing component 212 can include switching circuitry for selecting which of tip electrodes 112a,b, ring electrodes 114a,b and housing 1106 are coupled to sense amplifiers or other cardiac event detectors included in the electrical sensing component 212. Switching circuitry can include, for example, a switch array, a switch matrix, a multiplexer, or any other type of switching device suitable to selectively couple sense amplifiers to selected electrodes.

In some examples, the electrical sensing component 212 can include multiple sensing channels for sensing multiple electrocardiogram (ECG) sensing vectors selected from tip electrodes 112a,b, ring electrodes 114a,b and/or the housing 106. For example, the electrical sensing component 212 can include two sensing channels. Each sensing channel can include a sense amplifier or other cardiac event detection circuitry for sensing cardiac events, e.g., R-waves, from the received ECG signal developed across selected electrodes (e.g., tip electrodes 112a,b and/or ring electrodes 114a,b). The cardiac event detector can operate using an auto-adjusting sensing threshold set based on a peak amplitude of a currently sensed event that can decay over time. Each time the received ECG signal crosses the auto-adjusting sensing threshold outside an absolute blanking period, a cardiac sensed event signal, such as an R-wave sensed event signal, can be produced and passed to the control component 208 for use in detecting ventricular tachycardia (VT).

The control component 208 can be configured, for example, to detect VT episodes that may be life-threatening if left untreated (generally referred to herein as a "shockable rhythm") such as, for example, non-sinus VT, ventricular fibrillation, etc. The timing of R-wave sensed event signals received from the electrical sensing component 212 can be used by the control component 208 to determine R wave to R wave intervals between cardiac sensed event signals. The control component 208 can, for example, count RR intervals that fall into different rate detection zones for determining a ventricular rate or performing other rate- or interval-based assessments for detecting VT and discriminating VT from rhythms that do not require a CV/DF shock.

The electrical sensing component 212 can additionally or alternatively include an analog-to-digital converter that provides a digital ECG signal from one or all available sensing channels to the control component 208 for further signal analysis for use in VT detection. A sensed ECG signal can be converted to a multi-bit digital signal by the electrical sensing component 212 and provided to the control component 208 for performing ECG morphology analysis. Analysis of the ECG signal morphology can be performed for detecting, confirming or discriminating VT.

In an embodiment, the therapy delivery component 210 can include a high voltage (HV) therapy delivery module including one or more HV output capacitors and, in some instances, a low voltage therapy delivery module. When a shockable VT rhythm is detected, the HV output capacitors can be charged to a predefined voltage level by a HV charging circuit. The control component 208 can, for example apply a signal to trigger discharge of the HV capacitors upon detecting a feedback signal from the therapy delivery component 210 that the HV capacitors have reached the voltage required to deliver a programmed shock energy. In this way, the control component 208 can control operation of the high voltage output circuit of the therapy delivery component 210 to deliver high energy cardioversion/defibrillation shocks using tip electrodes 112a,b, ring electrodes 114a,b and/or the housing 106.

Each sensing channel included in the electrical sensing component 212 can include spike detector circuitry for detecting non-physiological electrical signal spikes present in the cardiac electrical(s) received by the electrical sensing component 212. The spike detector can produce a spike detect signal passed to the control component 208 for use in detecting a lead issue as well as avoiding false detections of VT due to oversensing of electrical spikes that are not true R-waves. In some examples, the electrical sensing component 212 can be configured to detect pacing pulses delivered to the body 102. For example, bradycardia pacing pulses or anti-tachycardia pacing pulses delivered by the implantable device 104 may be detected by the spike detector of the electrical sensing component 212.

Figure 3:
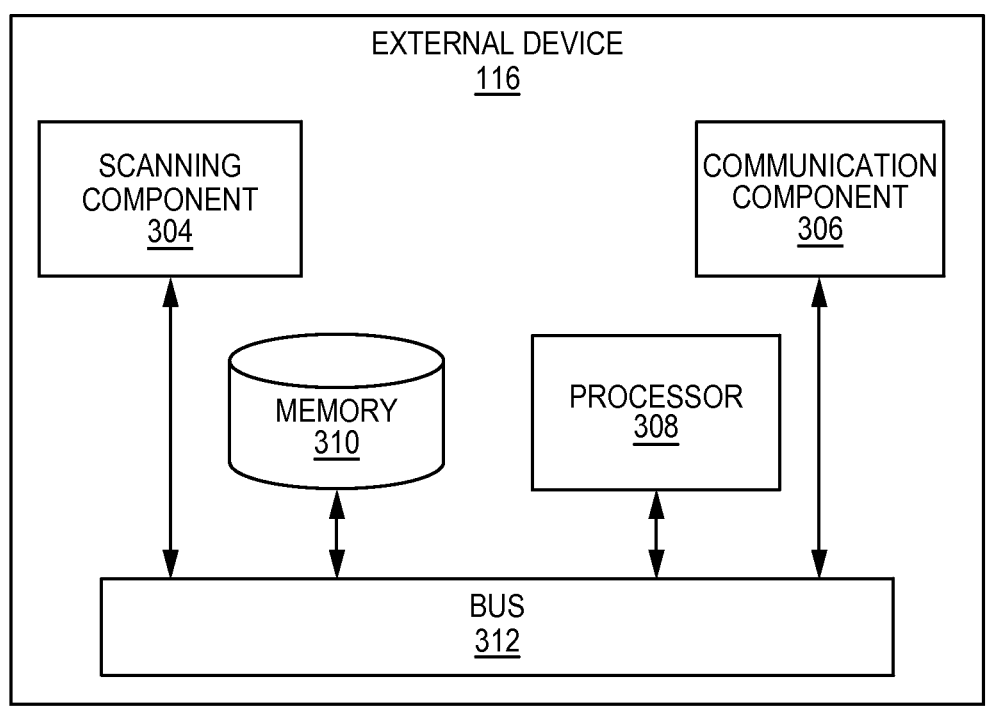
FIG. 3 illustrates a block diagram of an example, non-limiting external device in accordance with one or more embodiments described herein.

FIG. 3 illustrates a block diagram of an example, non-limiting external device (e.g., external device 116) in accordance with one or more embodiments described herein. The external device 116 includes a scanning component 304 and a communication component 306. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. External device 116 can include memory 310 for storing computer executable components and instructions. External device 116 can further include a processor 308 to facilitate operation of the instructions (e.g., computer executable components and instructions) by external device 116. External device 116 can include a bus 312 that couples the various components of the external device 116, including, but not limited to, the scanning component 304, the communication component 306, the processor 308 and/or the memory 310. Repetitive description of like elements employed in other embodiments described herein is omitted for sake of brevity.

The scanning component 304 can scan for one or more service fields (e.g., one or more service fields selected by the implantable device 104) of an advertising data packet associated with an implantable device (e.g., implantable device 104) via at least one advertising communication channel. For example, the scanning component 304 can passively scan for one or more service fields (e.g., one or more service fields selected by the implantable device 104) of an advertising data packet associated with an implantable device (e.g., implantable device 104) without transmitting data to the implantable device 104. In various embodiments, the scanning component 304 can scan a first advertising communication channel (e.g., a 2402 MHz communication channel), a second advertising communication channel (e.g., a 2426 MHz communication channel) and/or a third advertising communication channel (e.g., a 2480 MHz communication channel) for a service field included in a set of defined service fields (e.g., a set of defined UUIDs). In embodiments in which two or more channels are scanned, the particular advertising channels can be scanned in any order. The set of defined service fields can be associated with an implantable device (e.g., implantable device 104).

In some embodiments, the scanning component 304 can scan for and/or identify one or more UUIDs included in the advertising data packet. In one embodiment, the scanning component 304 can store and/or receive information identifying one or more defined service fields or a set of defined service fields associated with the implantable device 104. Therefore, the scanning component 304 can determine whether a defined service field from the set of defined service fields is included in an advertising data packet.

In another embodiment, the scanning component 304 can decode a defined service field that is identified in an advertising data packet. For example, the scanning component 304 can employ a data structure (e.g., a table data structure or a mapping data structure) that maps each defined service field from the set of defined service fields to information associated with the implantable device 104. The data structure can be stored, for example, in the memory 310 and/or in another memory. The scanning component 304 can scan (e.g., passively scan) for the one or more service fields (e.g., the one or more defined service fields) without connecting to an implantable device (e.g., the implantable device 104). Therefore, since the implantable device 104 can communicate information associated with the implantable device 104 to the external device 116 without establishing a connection with the external device 116 and/or without receiving one or more data packets from the external device 116, power associated with one or more power sources in the implantable device 104 can be conserved.

The communication component 306 can establish a communication link with the implantable device 104 via a communication channel different than the advertising communication channel in response to a determination that a criterion associated with a service field of the one or more service fields is satisfied. A criterion associated with a service field can be, for example, that the service field is included in a set of defined service fields associated with and/or generated for the implantable device 104. In one example, the communication component 306 can establish a communication link with the implantable device 104 via a communication channel different than the advertising communication channel in response to a determination that the implantable device 104 is ready to communicate information to an external device (e.g., the external device 116). In some embodiments, the communication component 306 can establish a communication link with the implantable device 104 via a communication channel different than the advertising communication channel in response to a determination that a particular service field from the set of defined service is identified (e.g., in response to a determination that an advertising data packet includes encoded information associated with the implantable device 104 and/or generated by the data packet component 204).

The communication component 306 can establish a communication link with the implantable device 104, for example, in response to a determination that a service field of an advertising data packet includes information, such as, but not limited to, a status of the implantable device 104, a communication status of the implantable device 104, a device status of the implantable device 104, power status information associated with the implantable device 104, a battery status associated with the implantable device 104, a processing status associated with the implantable device 104, a mode currently being implemented by the implantable device 104, other device status information associated with the implantable device 104, an alert (e.g., an alert status) associated with the implantable device 104, an indicator (e.g., an indicator status) associated with the implantable device 104, information associated with presence of the implantable device 104, medical data associated with the implantable device 104, fitness data associated with the implantable device 104, patient data for a patient associated with the implantable device 104, etc. In another embodiment, the communication component 306 can establish a communication link with the implantable device 104 based on content of information contained in an advertising data packet. The information contained in the advertising data packet can indicate whether the implantable device 104 has data to transmit and/or whether the implantable device 104 has experienced an event, for example.

In one embodiment, the scanning component 304 can determine that a service field of an advertising data packet includes the information by employing a data structure (e.g., a table data structure or a mapping data structure) that maps one or more (or, in some embodiments, each) defined service field from the set of defined service fields to information associated with the implantable device 104. In another embodiment, the scanning component 304 can decode the information from a service field by employing a data structure (e.g., a table data structure or a mapping data structure) that maps a defined service field from the set of defined service fields to information associated with the implantable device 104. Accordingly, the communication component 306 in connection with the communication component 206 can facilitate pairing the implantable device 104 and the external device 116 (e.g., setting up a communication channel between the implantable device 104 and the external device 116).

The communication component 306 can also forgo establishing a communication link with the implantable device 104 in response to a determination that a criterion associated with a service field of the one or more service fields is not satisfied. For example, communication component 306 can also forgo establishing a communication link with the implantable device 104 in response to a determination that the advertising data packet does not include information of interest in a particular service field and/or particular information for which the external device 116 may be searching. As such, the communication component 306 can forgo establishing a communication link with the implantable device 104 in response to a determination that the implantable device 104 is not ready to communicate information to an external device (e.g., the external device 116).

Figure 4:
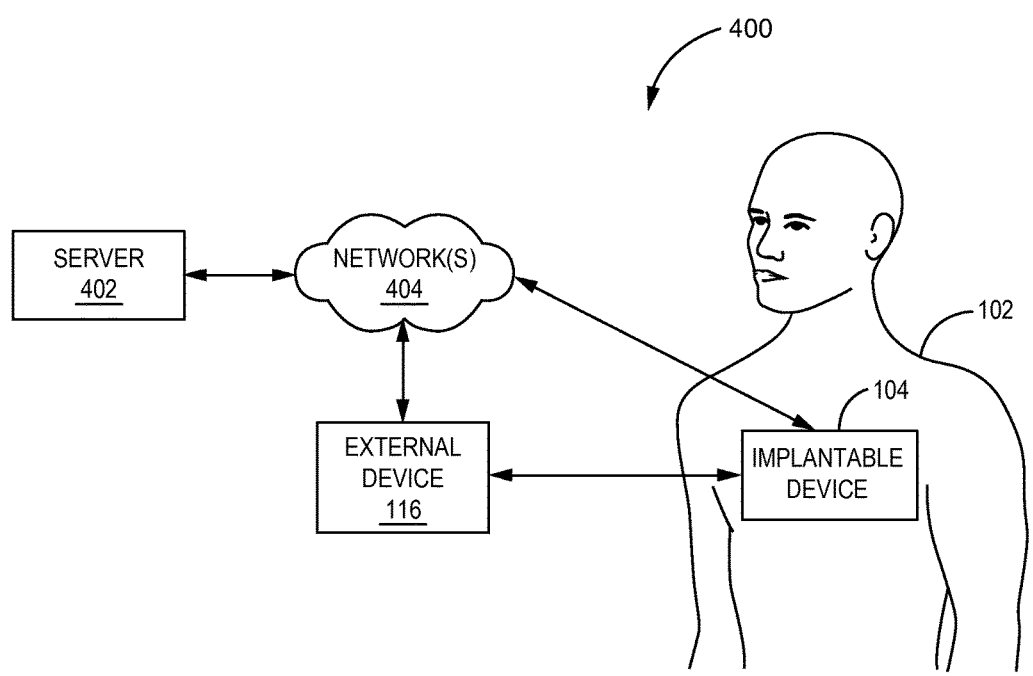
FIG. 4 illustrates an example schematic diagram of an example, non-limiting medical device telemetry system with a server facilitating communication between an implantable device and an external device in accordance with one or more embodiments described herein.

FIG. 4 illustrates an example schematic diagram of an example, non-limiting medical device telemetry system with a server facilitating communication between an implantable device and an external device in accordance with one or more embodiments described herein. In the embodiment shown, medical device telemetry system 400 includes the implantable device 104 implanted within the body 102 of the patient, the external device 116 and a server 402. Repetitive description of like elements employed in other embodiments described herein is omitted for sake of brevity.

In various aspects, the implantable device 104, the external device 116 and/or the server 402 are configured to communicate with one another over one or more networks 404. By way of example, the implantable device 104 and/or the external device 116 can communicate with the server 402 using a local area network (LAN), personal area network (PAN) or a wide area network (WAN) such as the Internet. Accordingly, one or more networks 404 can include various wired and/or wireless networks including, but not limited to, cellular networks, a network that facilitates BLE communication or the like.

In some embodiments, the server 402 can be a data server that stores content for one or more service fields and/or information related to one or more service fields. For example, the server 402 can generate and/or store a data structure (e.g., a table data structure or a mapping data structure) that maps one or more (or, in some embodiments, each) defined service fields from the set of defined service fields to information associated with the implantable device 104. The data structure generated and/or stored by the server 402 can be employed by the implantable device 104 and/or the external device 116.

The implantable device 104 and/or the external device 116 can receive the information for the set of defined service fields via the one or more networks 404. In an embodiment, the server 402 can be configured to randomly generate information for at least one service field included in the set of defined service fields. For example, the server 402 can include a random number generator and/or other circuitry, hardware and/or software configured to randomly generate information for at least one service field included in the set of defined service fields. A service field included in the set of defined service fields can include a randomly generated UUID, for example.

In certain embodiments, the server 402 can transmit information for the one or more service fields to the implantable device 104 via the one or more networks 404 (e.g., the implantable device 104 can receive one or more service fields from the server 402 via the one or more networks 404). In one example, the information for the one or more service fields transmitted to the implantable device 104 via the one or more networks 404 can be randomly generated information. In another example, the server 402 can transmit information for the one or more service fields to the implantable device 104 to configure and/or update a set of defined service fields stored on the implantable device 104. Additionally or alternatively, the server 402 can transmit the information for the one or more service fields to the external device 116 via the one or more networks 404 (e.g., the external device 116 can receive the information for the one or more service fields from the server 402 via the one or more networks 404). In one example, the information can be randomly generated.

In some embodiments, the information for the one or more service fields can be transmitted to the implantable device 104 and the external device 116 concurrently. In some embodiments, the information for the one or more service fields can be transmitted to the implantable device 104 and the external device 116 during non-overlapping periods of time. In yet another embodiment, the information transmitted to the implantable device 104 and/or the external device 116 can expire after a particular period of time and/or new information for one or more new service fields can be transmitted to the implantable device 104 and/or the external device 116 after the expiration of previously-transmitted information.

In a non-limiting example, a set of service UUIDs (e.g., a pool of service UUIDs) can be generated by the implantable device 104 and/or the server 402. The set of service UUIDs can be generated for the implantable device 104. Furthermore, the implantable device 104 and/or the server 402 can store the set of service UUIDs. The server 402 can additionally generate and/or store another set of service UUIDs for another implantable device. The implantable device 104 (e.g., the data packet component 204) can select a service UUID from the set of service UUIDs (e.g., to use in an advertising data packet generated by the communication component 206) based on information associated with the implantable device 104. The external device 116 (e.g., the scanning component 304) can therefore be configured to only scan for a subset of UUIDs (e.g., the set of UUIDs generated for the implantable device 104). Furthermore, the external device 116 can be configured to only connect to the implantable device 104 if a service UUID included in an advertising data packet generated by the implantable device 104 (e.g., generated by the data packet component 204) indicates that a particular condition is satisfied (e.g., the implantable device 104 is ready to transmit information to the external device 116). Accordingly, power source consumption (e.g., battery power consumption) of the implantable device 104 can be reduced by reducing or eliminating unnecessary connections with the external device 116. Moreover, in some embodiments, information representing an electronic flag (e.g., a manufacturer specific electronic flag) is therefore not required in an advertising data packet, which can improve compatibility with various external devices associated with a BLE protocol (e.g., off-the-shelf external devices associated with a BTLE protocol).

Figure 5:
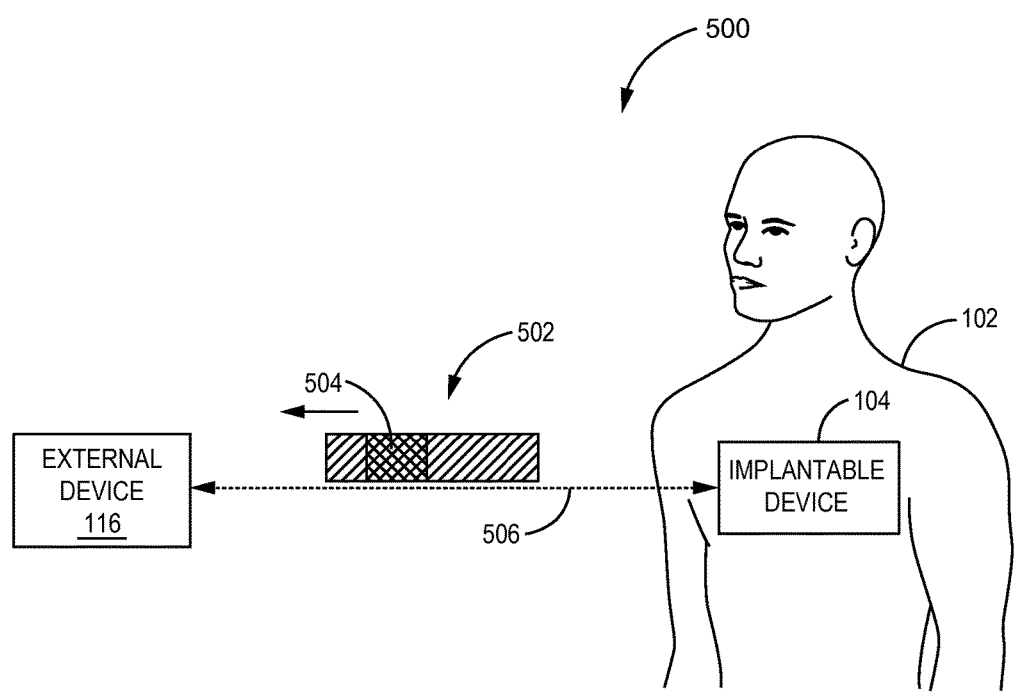
FIG. 5 illustrates an example, non-limiting medical device telemetry system facilitating communication between an implantable device and an external device based on an advertising data packet in accordance with one or more embodiments described herein.

FIG. 5 illustrates an example, non-limiting medical device telemetry system facilitating communication between an implantable device and an external device based on an advertising data packet in accordance with one or more embodiments described herein. Medical device telemetry system 500 includes the implantable device 104 and the external device 116. In some embodiments, as shown, the system 500 can also include a server such as server 402 of FIG. 4. Repetitive description of like elements employed in other embodiments described herein is omitted for sake of brevity.

The implantable device 104 can generate and transmit or broadcast an advertising data packet 502 that includes information in at least one service field 504. In various embodiments, any number of different service fields can be included in the advertising data packet 502.

In some embodiments, the data packet component 204 can insert information associated with the implantable device 104 into the service field 504 (e.g., the data packet component 204 can encode and/or generate information associated with the implantable device 104 in the service field 504). For example, the service field 504 can include information, such as, but not limited to, that which is: indicative of a status of the implantable device 104, information indicative of a communication status of the implantable device 104, indicative of a device status of the implantable device 104, indicative of power status information associated with the implantable device 104, indicative of a battery status associated with the implantable device 104, indicative of a processing status associated with the implantable device 104, indicative of a mode currently being executed by the implantable device 104, indicative of other device status information associated with the implantable device 104, indicative of an alert (e.g., an alert status) associated with the implantable device 104, indicative of an indicator (e.g., an indicator status) associated with the implantable device 104, associated with presence of the implantable device 104, etc. The service field 504 can therefore enable information associated with the implantable device 104 to be communicated to the external device 116 via the advertising data packet 502 (using only a UUID field, for example).

In one example, the service field 504 can be included in a packet data unit portion of the advertising data packet 502. The packet data unit portion of the advertising data packet 502 can be a payload portion of the advertising data packet 502. In some embodiments, the packet data unit portion can be a portion of the advertising data packet 502 associated with a low power communication protocol, such as BLE.

It is to be appreciated that the location of the service field 504 within the advertising data packet 502 can differ from time to time. For example, content of the service field 504 can be varied (e.g., dynamic) based on the status or other information associated with the implantable device 104. In some embodiments, a portion of the advertising data packet 502 can be static and another portion of the advertising data packet (e.g., for example, the portion associated with the service field 504) can be dynamic.

The implantable device 104 can transmit and/or broadcast the advertising data packet 502 that includes the service field 504 via an advertising communication channel 506. In one embodiment, the implantable device 104 can repeatedly transmit the advertising data packet 502 that includes the service field 504 via the advertising communication channel 506 during a defined period of time. In another embodiment, the advertising communication channel 506 shown in FIG. 5 can represent a set of advertising communication channels. For example, the advertising data packet 502 can be broadcasted via the advertising communication channel 506 and one or more other advertising communication channels. In one example, the advertising communication channel 506 can be an advertising channel associated with a BLE protocol. For example, the advertising data packet 502 can be transmitted as a bit stream that is grouped into a set of code words. In one example of system 500, the implantable device 104 can be implemented as an advertiser device and the external device 116 can be implemented as a scanner device.

Figure 6:
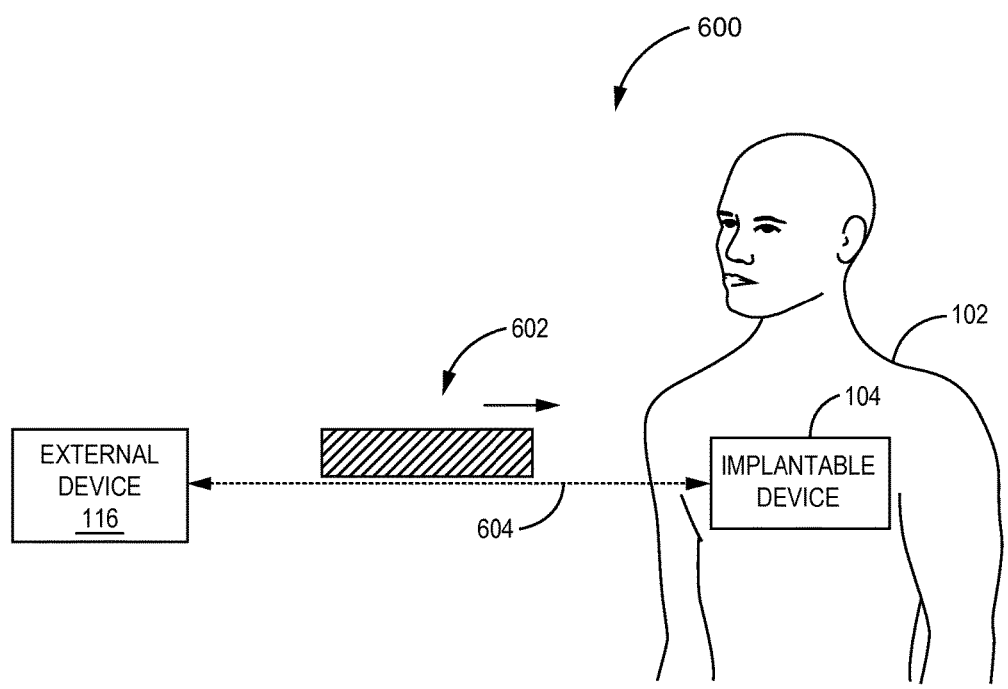
FIG. 6 illustrates an example, non-limiting medical device telemetry system facilitating communication between an implantable device and an external device based on a response data packet in accordance with one or more embodiments described herein.

FIG. 6 illustrates an example, non-limiting medical device telemetry system facilitating communication between an implantable device and an external device based on a response data packet in accordance with one or more embodiments described herein. Medical device telemetry system 600 includes the implantable device 104 and the external device 116. In certain embodiments, the system 600 can also include the server 402 illustrated in FIG. 4. Repetitive description of like elements employed in other embodiments described herein is omitted for sake of brevity.

In response to the implantable device 104 transmitting and/or broadcasting the advertising data packet 502 via the advertising communication channel 506, the external device 116 can generate a response data packet 602. The external device 116 can transmit the response data packet 602 via a communication channel 604 that is different than the advertising communication channel 506 (shown and described with reference to FIG. 5). The response data packet 602 can facilitate establishment of a communication link (e.g., active communication) between the implantable device 104 and the external device 116. Therefore, the advertising data packet 502 (e.g., the service field 504 of the advertising data packet 502) can enable information associated with the implantable device 104 to be communicated to the external device 116 before a response data packet (e.g., the response data packet 602) is generated and/or before a communication link (e.g., an active communication) between the implantable device 104 and the external device 116 is established via a response data packet (e.g., the response data packet 602).

In some embodiments, the implantable device 104 can transmit data (e.g., one or more data packets) to the external device 116 via the communication channel 604 and/or another communication channel in response to receiving the response data packet 602 from the external device 116. For example, the implantable device 104 can actively communicate data to the external device 116 via the communication channel 604 and/or another communication channel in response to receiving the response data packet 602 from the external device 116.

FIGS. 7-10 illustrate flow diagrams of example, non-limiting methods facilitating communication between an implantable device and an external device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 7:
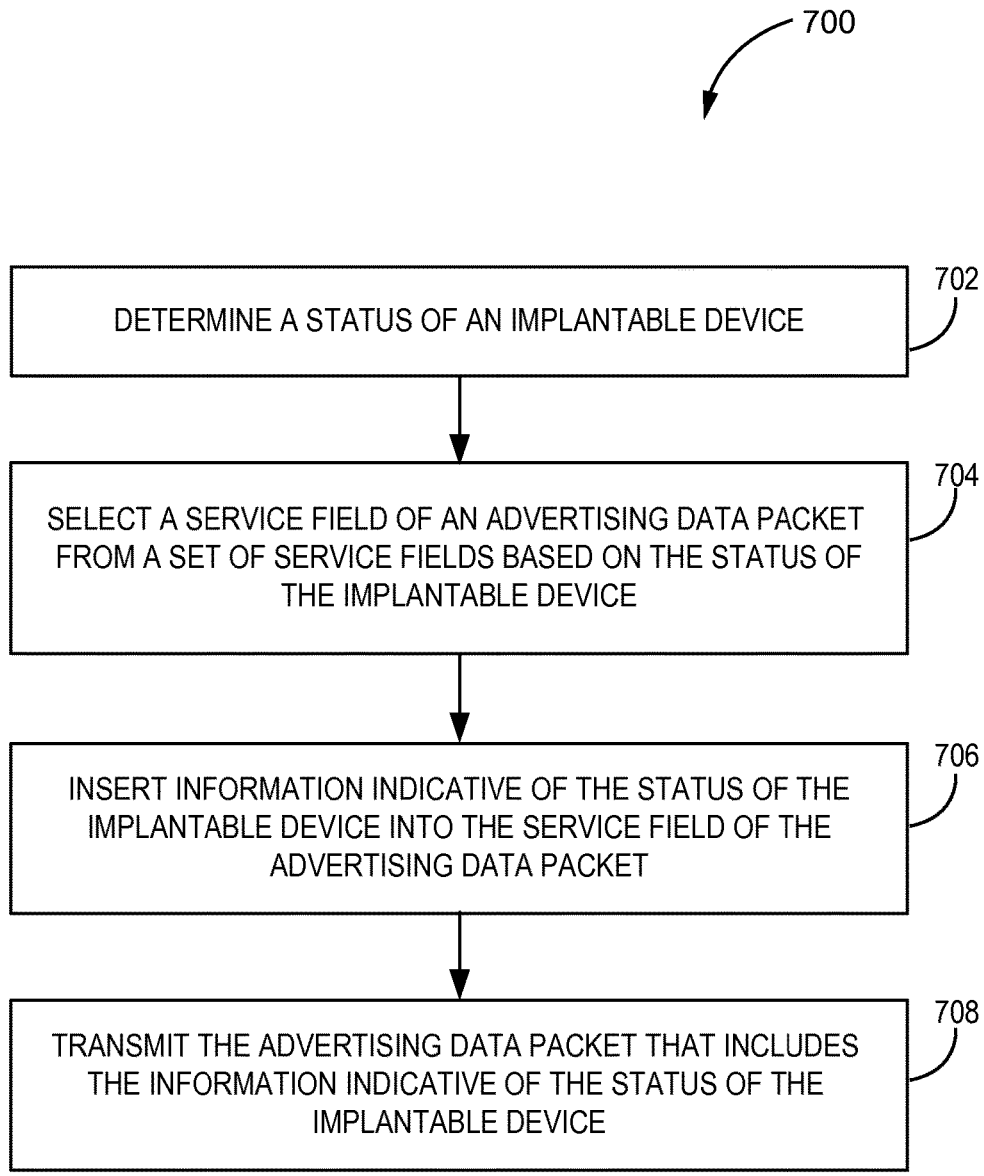
FIGS. 7-10 illustrate flow diagrams of example, non-limiting methods facilitating communication between an implantable device and an external device in accordance with one or more embodiments described herein.

Referring now to FIG. 7, shown is a flow diagram of an example method 700 facilitating communication between an implantable device and an external device in accordance with one embodiment. In some embodiments of method 700, an implantable device (e.g., implantable device 104) employs a data packet component (e.g., data packet component 204) and/or a communication component (e.g., communication component 206) to facilitate communication between an implantable device and an external device. Repetitive description of like elements employed in other embodiments described herein is omitted for sake of brevity.

At 702, a status of an implantable device can be determined (e.g., by the data packet component 204). For example, a status of the implantable device, a device status of the implantable device and/or other information associated with the implantable device can be determined. In one example, a status of the implantable device and/or other information associated with the implantable device can be retrieved from memory. In another example, a status of the implantable device and/or other information associated with the implantable device can be received from component of the implantable device (e.g., a processor). The implantable device can be, for example, an IMD.

At 704, a service field of an advertising data packet can be selected from a set of service fields (e.g., by the data packet component 204) based on the status of the implantable device. For example, a set of defined service fields can be generated for the implantable device. As such, a service field from the set of defined service fields generated for the implantable device can be selected based on the status of the implantable device. In one example, the set of defined service fields can be a set of defined identifiers (e.g., UUIDs, etc.).

At 706, information indicative of the status of the implantable device can be inserted (e.g., by the data packet component 204) into the service field of the advertising data packet. For example, the information indicative of the status of the implantable device can be encoded as a UUID. In another example, the information indicative of the status of the implantable device can be encoded as a hexidecimal value. In yet another example, the information indicative of the status of the implantable device can be encoded as a bit value that is greater than or equal to a 16-bit value.

At 708, the advertising data packet that includes the information indicative of the status of the implantable device can be transmitted (e.g., by the communication component 206). For example, the advertising data packet that includes the information indicative of the status of the implantable device can be broadcasted (e.g., repeatedly broadcasted via a set of advertising communication channels) during a defined period of time. The advertising data packet that includes the information indicative of the status of the implantable device can be transmitted via an advertising communication channel (e.g., a wireless advertising communication channel).

Because configuration of a data packet and communication between the implantable device (e.g., the implantable device 104) and the external device (e.g., the external device 116) is established from a combination of electrical and mechanical components and circuitry, and due to the inserting (e.g., encoding) of information associated with the implantable device (e.g., the implantable device 104) within a service field as described herein, a human is unable to replicate or perform the subject data packet configuration and/or the subject communication between the implantable device and the external device. For example, a human is unable to encode information indicative of the status of the implantable device in the service field of the advertising data packet, transmit the advertising data packet (e.g., via an advertising communication channel), etc. For example, a human is unable to packetize a data packet that includes a sequence of bits corresponding to information indicative of the status of the implantable device, a human cannot wirelessly broadcast a data packet at a particular frequency via a communication channel, etc.

Figure 8:
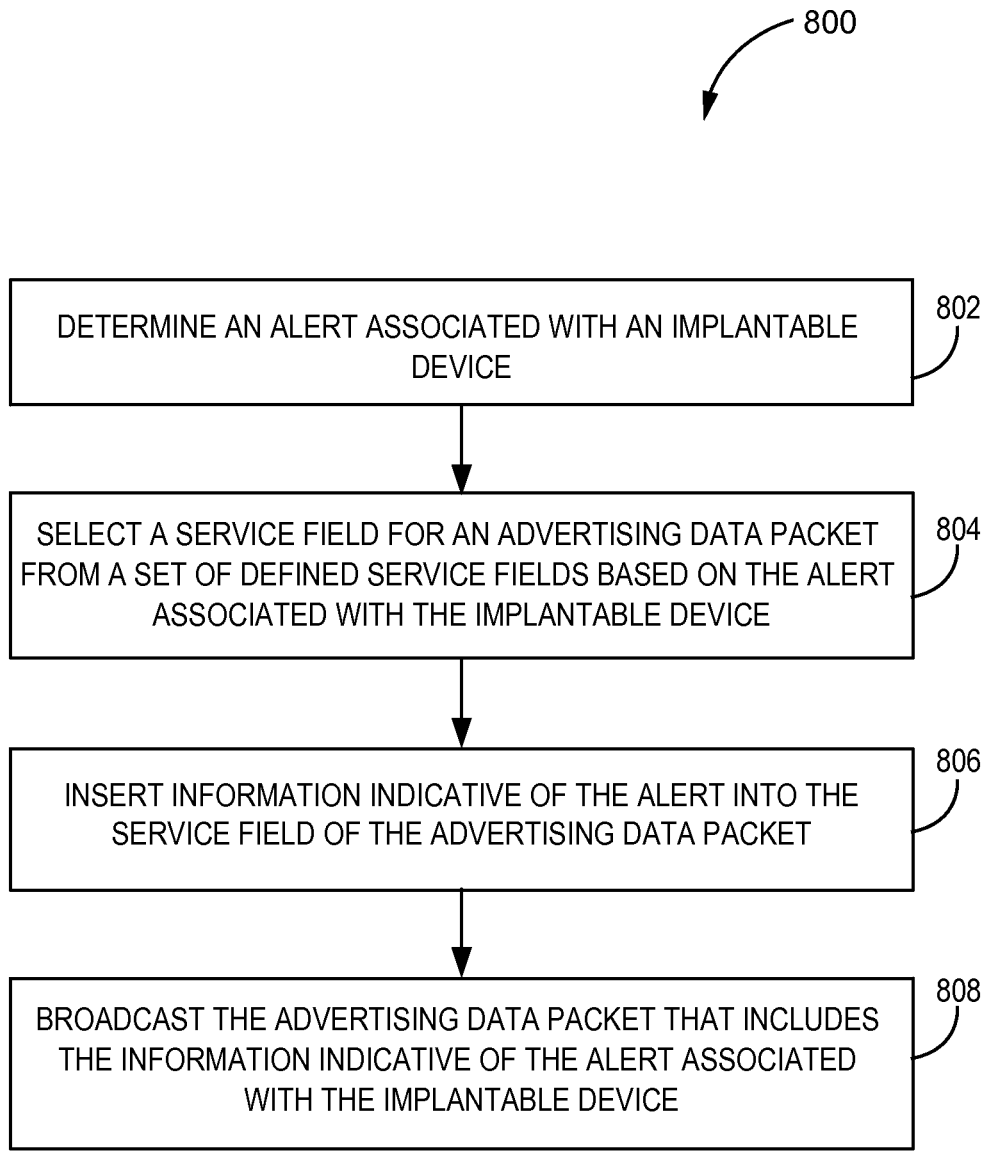

Turning now to FIG. 8, shown is another method 800 for facilitating communication between an implantable device and an external device. In some embodiments of method 800, an implantable device (e.g., implantable device 104) employs a data packet component (e.g., data packet component 204) and/or a communication component (e.g., communication component 206) to facilitate communication between an implantable device and an external device. Repetitive description of like elements employed in other embodiments described herein is omitted for sake of brevity.

At 802, an alert associated with an implantable device can be determined (e.g., by the data packet component 204). For example, an alert status or an indicator status associated with the implantable device can be determined. However, it is to be appreciated that other information associated with the implantable device can additionally or alternatively be determined. For example, other information associated with the implantable device can include, but is not limited to, a status of the implantable device, a communication status of the implantable device, a device status of the implantable device, power status information associated with the implantable device, a battery status associated with the implantable device, a processing status associated with the implantable device, a mode being implemented by the implantable device, other device status information associated with the implantable device, information associated with presence of the implantable device, medical data associated with the implantable device, fitness data associated with the implantable device, patient data for a patient associated with the implantable device, etc. At 804, a service field for an advertising data packet can be selected from a set of defined service fields (e.g., by the data packet component 204) based on the alert associated with the implantable device. At 806, information indicative of the alert can be inserted into the service field of the advertising data packet (e.g., by the data packet component 204). For example, the information indicative of the alert associated with the implantable device can be encoded as a UUID. In another example, the information indicative of the alert associated with the implantable device can be encoded as a hexidecimal value. In yet another example, the information indicative of the alert associated with the implantable device can be encoded as a bit value that is greater than or equal to a 16-bit value. At 808, the advertising data packet that includes the information indicative of the alert associated with the implantable device can be broadcasted (e.g., by the communication component 206). For example, the advertising data packet that includes the information indicative of the status of the implantable device can be transmitted (e.g., repeatedly transmitted via a set of advertising communication channels) during a defined period of time. Because selection and/or decoding of electronic information in the service field is performed from a combination of electrical and mechanical components and circuitry, a human is unable to replicate or perform these operations.

Figure 9:
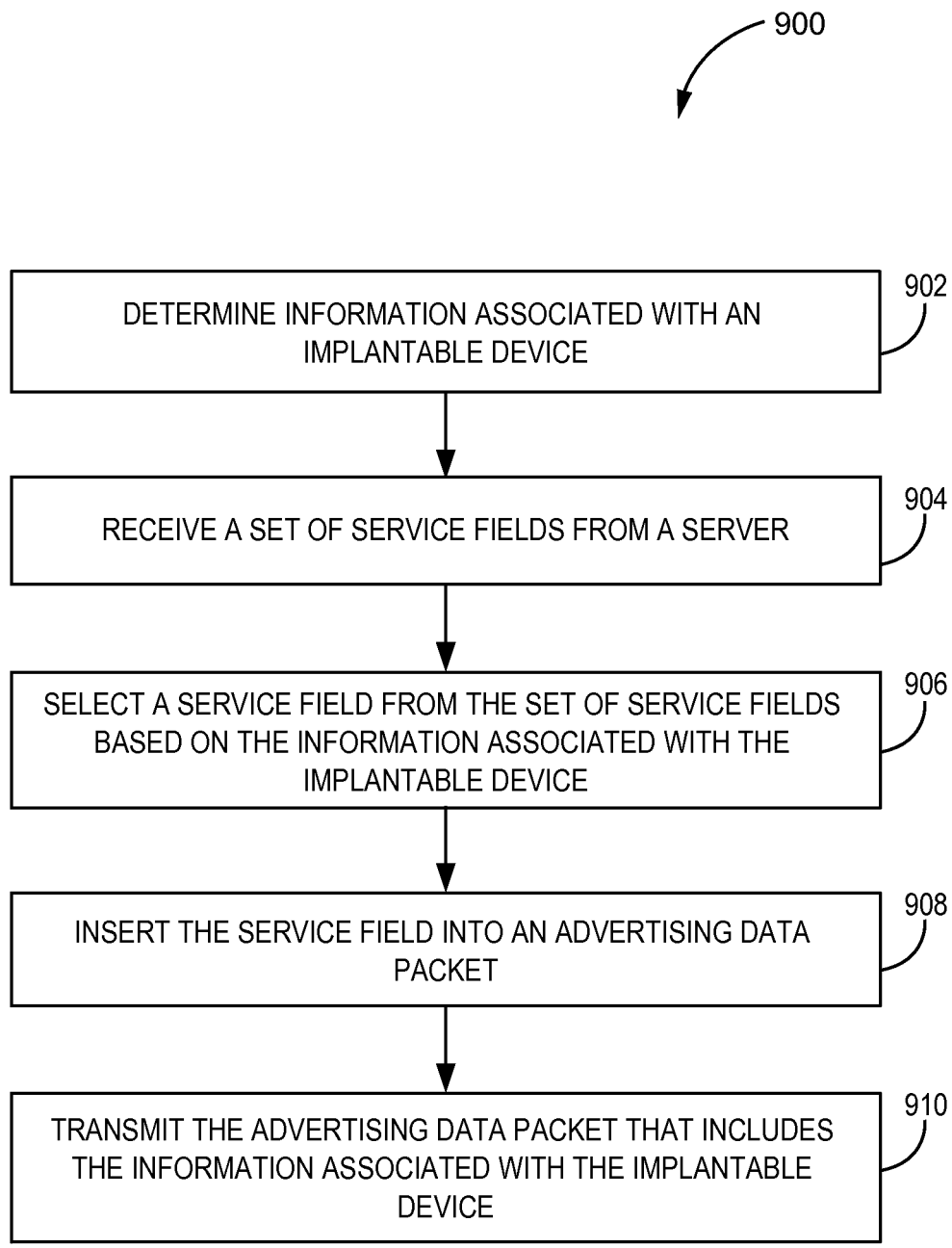

Turning now to FIG. 9, shown is another method 900 for facilitating communication between an implantable device and an external device. In some embodiments of method 900, an implantable device (e.g., implantable device 104) employs a data packet component (e.g., data packet component 204) and/or a communication component (e.g., communication component 206) to facilitate communication between an implantable device and an external device. Repetitive description of like elements employed in other embodiments described herein is omitted for sake of brevity.

At 902, information associated with an implantable device can be determined (e.g., by the data packet component 204). For example, the information associated with the implantable device can include, but is not limited to, information indicative of a status of the implantable device, a communication status of the implantable device, a device status of the implantable device, power status information associated with the implantable device, a battery status associated with the implantable device, a processing status associated with the implantable device, a mode currently being implemented by the implantable device, other device status information associated with the implantable device, an alert (e.g., an alert status) associated with the implantable device, an indicator (e.g., an indicator status) associated with the implantable device, information associated with presence of the implantable device, etc.

At 904, a set of service fields can be received from a server (e.g., the data packet component 204 can receive a set of service fields from a server). For example, the server can generate and/or store a set of defined service fields. In one example, the server can randomly generate one or more service fields (e.g., one or more service field values) included in the set of defined service fields. The set of service fields can be received over a wireless communication channel, for example. In an implementation, the set of service fields can be received during a previous communication session with the server and/or stored in memory. At 906, a service field from the set of service fields can be selected based on the information associated with the implantable device. For example, a service field value that corresponds to the information associated with the implantable device can be selected from the set of service fields received from the server. At 908, the service field can be inserted into an advertising data packet (e.g., by the data packet component 204). For example, the service field can be encoded in the advertising data packet. At 910, the advertising data packet that includes the information associated with the implantable device can be transmitted (e.g., by the communication component 206). For example, the advertising data packet that includes the information associated with the implantable device can be transmitted (e.g., repeatedly transmitted via a set of advertising communication channels) during a defined period of time. Because reception and/or processing of signals over a wireless channel, and selection of electronic information in the service field are performed from a combination of electrical and mechanical components and circuitry, a human is unable to replicate or perform these operations.

Figure 10:
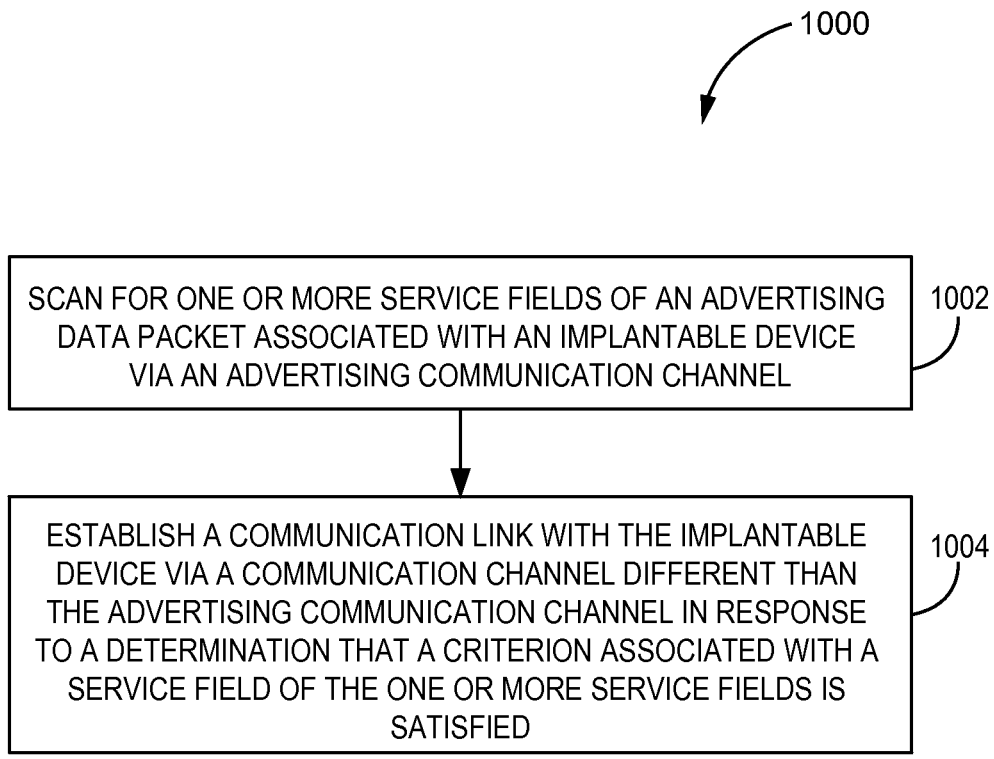

FIG. 10 shows a method 1000 for facilitating communication between an implantable device and an external device. In some embodiments of method 1000, an external device (e.g., external device 116) employs a scanning component (e.g., scanning component 304) and/or a communication component (e.g., communication component 306) to facilitate communication between an implantable device and an external device. Repetitive description of like elements employed in other embodiments described herein is omitted for sake of brevity.

At 1002, one or more service fields of an advertising data packet associated with an implantable device can be scanned via an advertising communication channel. For example, the scanning component 304 can scan one or more service fields of an advertising data packet associated with an implantable device via an advertising communication channel. In one example, a set of service fields can be defined for the implantable device. As such, one or more advertising communication channels can be monitored for a service field included in the set of service fields.

At 1004, a communication link with the implantable device can be established via a communication channel different than the advertising communication channel in response to a determination that a criterion associated with a service field of the one or more service fields is satisfied. For example, the communication component 306 can establish a communication link with the implantable device via a communication channel different than the advertising communication channel in response to a determination that a criterion associated with a service field of the one or more service fields is satisfied.

In one example, the communication link can be established in response to a determination that the implantable device is ready to communicate information. The information can include, for example, a status of the implantable device, a communication status of the implantable device, a device status of the implantable device, power status information associated with the implantable device, a battery status associated with the implantable device, a processing status associated with the implantable device, a mode currently being implemented by the implantable device, other device status information associated with the implantable device, an alert (e.g., an alert status) associated with the implantable device, an indicator (e.g., an indicator status) associated with the implantable device, information associated with presence of the implantable device, medical data associated with the implantable device, fitness data associated with the implantable device, patient data for a patient associated with the implantable device, other information, etc. In some embodiments, a communication link with the implantable device is not established in response to a determination that the criterion associated with a service field of the one or more service fields is not satisfied. Because scanning electronic information in the service field and establishing a wireless communication link with a device are performed from a combination of electrical and mechanical components and circuitry, a human is unable to replicate or perform these operations.

Figure 11:
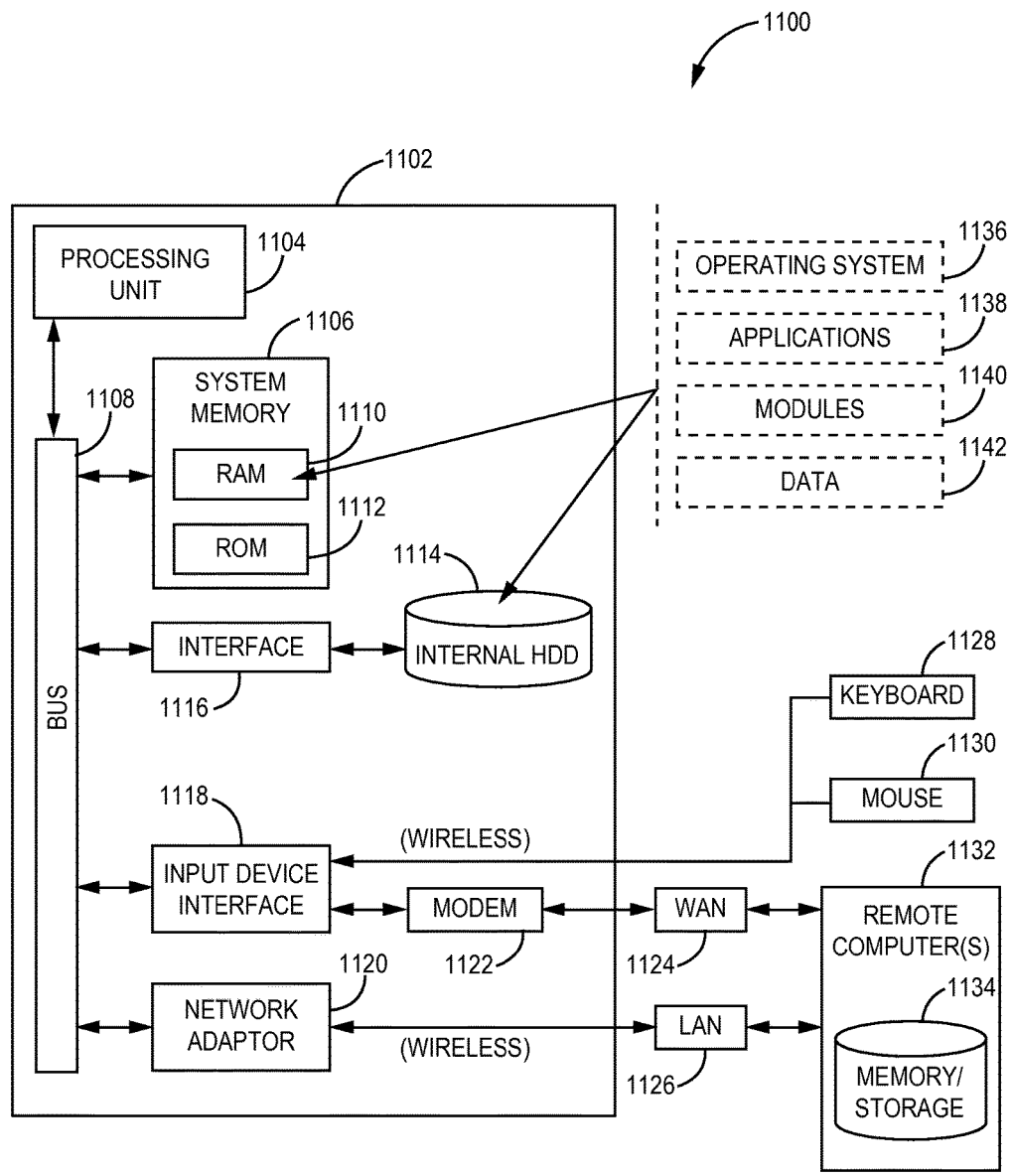
FIG. 11 illustrates a block diagram of an example, non-limiting computer operable to facilitate communication between an implantable device and an external device in accordance with one or more embodiments described herein.

FIG. 11 illustrates a block diagram of a computer operable to facilitate communication between an implantable device and an external device in accordance with one or more embodiments described herein. For example, in some embodiments, the computer can be or be included within implantable device 104, external device 116, and/or server 402 (or any component of the implantable device 104, external device 116 and/or server 402). Repetitive description of like elements employed in other embodiments described herein is omitted for sake of brevity.

In order to provide additional context for one or more embodiments described herein, FIG. 11 and the following discussion are intended to provide a brief, general description of a suitable computing environment 1100 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, example environment 1100 for implementing one or more embodiments of the embodiments described herein includes computer 1102, computer 1102 including processing unit 1104, system memory 1106 and system bus 1108. System bus 1108 couples system components including, but not limited to, system memory 1106 to processing unit 1104. Processing unit 1104 can be any of various commercially available processors. Dual microprocessors and other multi processor architectures can also be employed as processing unit 1104.

System bus 1108 can be any of several types of bus structure that can further interconnect to a memory bus (with or without a memory controller), a peripheral bus, and a local bus using any of a variety of commercially available bus architectures. System memory 1106 includes RAM 1110 and ROM 1112. A basic input/output system (BIOS) can be stored in a non-volatile memory such as ROM, erasable programmable read only memory (EPROM), EEPROM, which BIOS contains the basic routines that help to transfer information between elements within computer 1102, such as during startup. RAM 1110 can also include a high-speed RAM such as static RAM for caching data.

Computer 1102 further includes internal hard disk drive (HDD) 1114 (e.g., Enhanced Integrated Drive Electronics (EIDE), Serial Advanced Technology Attachment (SATA)). HDD 1114 can be connected to system bus 1108 by hard disk drive interface 1116. The drives and their associated computer-readable storage media provide nonvolatile storage of data, data structures, computer-executable instructions, and so forth. For computer 1102, the drives and storage media accommodate the storage of any data in a suitable digital format.

A number of program modules can be stored in the drives and RAM 1110, including operating system 1136, one or more application programs 1138, other program modules 1140 and program data 1142. All or portions of the operating system, applications, modules, and/or data can also be cached in RAM 1110. The systems and methods described herein can be implemented utilizing various commercially available operating systems or combinations of operating systems.

A mobile device can enter commands and information into computer 1102 through one or more wireless input devices, e.g., wireless keyboard 1128 and a pointing device, such as wireless mouse 1130. Other input devices (not shown) can include a smart phone, tablet, laptop, wand, wearable device or the like. These and other input devices are often connected to the processing unit 1104 through input device interface 1118 that can be coupled to system bus 1108, but can be connected by other interfaces, such as a parallel port, an IEEE serial port, a game port and/or a universal serial bus (USB) port.

Computer 1102 can operate in a networked environment using logical connections via wired and/or wireless communications to one or more remote computers, such as remote computer(s) 1132. Remote computer(s) 1132 can be a workstation, a server computer, a router, a personal computer, portable computer, microprocessor-based entertainment appliance, a peer device or other common network node, and typically includes many or all of the elements described relative to computer 1102, although, for purposes of brevity, only memory/storage device 1134 is illustrated. The logical connections depicted include wired/wireless connectivity to a local area network (LAN) 1126 and/or larger networks, e.g., WAN 1124, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1102 can be connected to local network through a wired and/or wireless communication network interface or adapter 1120. Adapter 1120 can facilitate wired or wireless communication to LAN 1126, which can also include a wireless access point (AP) connected to the LAN 1126 for communicating with adapter 1120.

When used in a WAN networking environment, computer 1102 can include modem 1122 or can be connected to a communications server on WAN 1124 or has other means for establishing communications over WAN 1124, such as by way of the Internet. Modem 1122, which can be internal or external and a wired or wireless device, can be connected to system bus 1108 via input device interface 1116. In a networked environment, program modules depicted relative to computer 1102 or portions thereof, can be stored in a remote memory/storage device. It will be appreciated that the network connections shown are example and other means of establishing a communications link between the computers can be used.

Computer 1102 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds.

Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable device, comprising:
a memory that stores executable components; and
a processor that executes the executable components stored in the memory, wherein the executable components comprise:
a data packet component configured to insert information associated with the implantable device in a defined service field of an advertising data packet, wherein the defined service field is selected from one or more service fields of the advertising data packet based on the information associated with the implantable device; and
a communication component configured to transmit the advertising data packet.

2. The implantable device of claim 1, wherein the data packet component is configured to encode the information associated with the implantable device as a universally unique identifier.

3. The implantable device of claim 1, wherein the data packet component is configured to encode the information associated with the implantable device as a bit value that is greater than or equal to a 16-bit value.

4. The implantable device of claim 1, wherein the data packet component is configured to insert information indicative of a status of the implantable device in the defined service field of the advertising data packet.

5. The implantable device of claim 4, wherein the data packet component is configured to insert information associated with presence of the implantable device in the defined service field of the advertising data packet.

6. The implantable device of claim 1, wherein the communication component is configured to sequentially transmit the advertising data packet via a set of advertising communication channels.

7. The implantable device of claim 1, wherein the communication component is configured to transmit the advertising data packet via an advertising communication channel associated with a communication protocol utilizing low energy consumption.

8. The implantable device of claim 1, wherein the communication component is further configured to establish, via a communication channel different than an advertising communication channel associated with the advertising data packet, a wireless communication link with an electronic device external to a body in which the implantable device is located.

9. The implantable device of claim 8, wherein the communication component is further configured to receive a response data packet from the electronic device in response to receipt of the advertising data packet by the electronic device.

10. The implantable device of claim 1, further comprising:
a therapy delivery component configured to output one or more electrical pulses to a region of a body in which the implantable device is located to facilitate medical treatment of a condition associated with the region of the body.

11. The implantable device of claim 1, further comprising:
an electrical sensing component configured to detect one or more electrical signals in a body in which the implantable device is located, wherein the one or more electrical signals is indicative of a medical condition of the body.

12. An apparatus, comprising:
a memory that stores executable components; and
a processor that executes the executable components stored in the memory, wherein the executable components comprise:
a scanning component configured to scan one or more service fields of an advertising data packet associated with an implantable device via an advertising communication channel; and
a communication component configured to establish a communication link with the implantable device via a communication channel different than the advertising communication channel in response to a determination that a criterion associated with a service field of the one or more service fields is satisfied.

13. The apparatus of claim 12, wherein the scanning component is further configured to identify one or more unique identifiers included in the advertising data packet.

14. The apparatus of claim 12, wherein the scanning component is further configured to scan for a defined one of the one or more service fields via the advertising communication channel.

15. The apparatus of claim 12, wherein the communication component is further configured to establish the communication link in response to a determination that information indicative of a status of the implantable device is included in the service field.

16. The apparatus of claim 12, wherein the communication component is further configured to establish the communication link in response to a determination that information indicative of an alert associated with the implantable device is included in the service field.

17. The apparatus of claim 12, wherein the communication component is further configured to establish the communication link in response to a determination that information associated with a presence of the implantable device is included in the service field.

18. A method, comprising:
determining, by a device comprising a processor, information associated with an implantable device;
selecting a service field of an advertising data packet from a set of service fields of the advertising data packet based on the information associated with the implantable device;
inserting the information associated with the implantable device into the service field of the advertising data packet; and
transmitting the advertising data packet.

19. The method of claim 18, wherein the inserting comprises encoding the information associated with the implantable device as a universally unique identifier.

20. The method of claim 18, wherein the inserting comprises encoding the information associated with the implantable device as a bit value that is greater than or equal to a 16-bit value.

21. The method of claim 18, wherein the inserting comprises inserting information indicative of a status of the implantable device in the service field of the advertising data packet.

22. The method of claim 21, wherein the inserting comprises inserting information indicative of medical data associated with the implantable device in the service field of the advertising data packet.

23. A system, comprising:
an apparatus configured to:
select a service field of an advertising data packet from one or more service fields of the advertising data packet based on a status of an implantable device;
generate first information indicative of a first status of the implantable device in the service field of the advertising data packet; and
transmit the advertising data packet during a defined interval of time; and
an electronic device configured to:
scan for the one or more service fields of the advertising data packet associated with the implantable device; and
establish a communication link with the implantable device in response to a determination about the first information indicative of the first status of the implantable device in the service field.

24. The system of claim 23, wherein the apparatus is further configured to receive second information for the one or more service fields from a server, wherein the second information differs from the first information and is indicative of a second status of the implantable device.

25. The system of claim 24, wherein the apparatus is further configured to update a mapping table of the apparatus with the second information indicative of the second status.

26. The system of claim 24, wherein the server is configured to randomly generate second information for the one or more service fields.

27. The system of claim 23, further comprising:
a server configured to randomly generate second information for the one or more service fields.

28. The system of claim 23, wherein the apparatus is configured to transmit the advertising data packet utilizing Bluetooth Low Energy communication protocol.

* * * * *